United States Patent [19]

Greig et al.

[11] Patent Number: 5,409,948
[45] Date of Patent: * Apr. 25, 1995

[54] METHOD FOR TREATING COGNITIVE DISORDERS WITH PHENSERINE

[75] Inventors: Nigel H. Greig, Silver Spring; Arnold Brossi, Bethesda; Timothy T. Soncrant, Silver Spring; Harold W. Holloway, Bethesda, all of Md.; Stanley I. Rapoport, Washington, D.C.; Setsu Iijima, Tokyo, Japan; Edward L. Spangler, Baltimore, Md.; Donald K. Ingram, Ellicott City, Md.; Xue F. Pei, Bethesda, Md.

[73] Assignee: The United States of America as represented by the Secretary of the Department of Health and Human Services, Washington, D.C.

[*] Notice: The portion of the term of this patent subsequent to Dec. 15, 2009 has been disclaimed.

[21] Appl. No.: 980,399

[22] Filed: Nov. 23, 1992

[51] Int. Cl.⁶ ............................................. A61K 31/40
[52] U.S. Cl. .................................................. 514/411
[58] Field of Search .......................................... 514/411

[56] References Cited

U.S. PATENT DOCUMENTS

| | | | |
|---|---|---|---|
| 4,791,107 | 12/1988 | Hamer et al. | 514/228.2 |
| 4,914,102 | 4/1990 | Glamkowski | 514/232.8 |
| 4,971,992 | 11/1990 | Glamkowski et al. | 514/411 |
| 4,996,201 | 2/1991 | Bergmeier et al. | 514/212 |
| 5,077,289 | 12/1991 | Glamkowski et al. | 514/211 |
| 5,081,117 | 1/1992 | Glamkowski et al. | 514/216 |
| 5,089,267 | 2/1992 | Hille et al. | 424/449 |
| 5,171,750 | 12/1992 | Brossi et al. | 514/411 |

OTHER PUBLICATIONS

M. Marta et al., "New Analogs of Physostigmine: Alternative Drugs for Alzheimer's Disease?", Life Science, vol. 43, No. 23, 1988, pp. 1921–1928.

Yu et al, "Carbamate Analogues of (−)-physostigmine: In Vitro Inhibition of Acetyl- and Butyrylcholinesterase", FEBS Letters vol. 234, No. 1, pp. 127–130, Jul., 1988.

Atack et al, "Comparative Inhibitory Effects of Various Physostigmine Analogs Against Acetyl- and Butyrylcholinsterases", Jour. of Pharmacology and Experimental Therapeutics, vol. 249:1, pp. 194–202, 1989.

Primary Examiner—Raymond Henley, III
Assistant Examiner—William R. A. Jarvis
Attorney, Agent, or Firm—Lowe, Price, LeBlanc & Becker

[57] ABSTRACT

An improved method of cholinomimetic therapy for cognitive impairments associated with aging and Alzheimer's disease comprising treating a patient with an effective amount of phenserine or a pharmaceutically acceptable salt and derivatives.

6 Claims, 9 Drawing Sheets

METHOD FOR TREATING COGNITIVE DISORDERS WITH PHENSERINE

This application is related to application Ser. No. 08/096,207 filed Jul. 26, 1992 which is a continuation of Ser. No. 07/861,329 filed Mar. 31, 1992, now abandoned, which is a divisional of application Ser. No. 07/765,746 filed Sep. 26, 1991 now U.S. Pat. No. 5,171,750.

TECHNICAL FIELD

The present invention relates to improvements in methods for the treatment of cognitive disorder diseases, and more particularly to physostigmine derivatives, i.e., phenserine and its salts, which are long-acting inhibitors of cholinesterase and demonstrate a wide dosage range for attenuating a scopolamine-induced learning impairment of rats in a 14-unit T-maze.

BACKGROUND ART

Physostigmines, also called eserines, are known cholinesterase inhibitors. These compounds are also useful in the treatment of glaucoma, Myasthenia Gravis, and Alzheimer's disease, and as antidotes against poisoning with organophosphates.

It has been discovered that the natural isomer of physostigmine has blocking properties as well as agonist properties at the neuromuscular AChR. By contrast, (+)-physostigmine shows only negligible inhibition of cholinesterase (ChE). See Brossi et al., FEBS Lett., Vol. 201, pages 190-192 (1986).

Even though (+)-physostigmine has only negligible ChE inhibitory activity, it is effective as a protective pretreatment drug against multiple lethal doses of sarin, see Albuquerque et al, Fundam. Appl. Caltoxicol., Vol. 5, pages 182-203 (1985). The observed beneficial protection appears to be due to direct interactions of the carbamates with the postsynaptic nicotinic AChR. The protective effectiveness of the carbamates against organophosphates appears to be related to the direct ability of the carbamates to decrease the hyperactivation caused by accumulation of the neurotransmitter.

The above information, is important in evaluation of potential new pharmacological agents for treating cholinergic disorders, for example, Myasthenia Gravis and Alzheimer's disease. Potential agents can be evaluated for potency in vitro by testing the agents against electric eel and human red blood cell acetylcholinesterase (AChE) and human plasma butyrylcholinesterase (BChE).

Since defects in the cholinergic system have been suggested to underlie cognitive impairments associated with normal aging and Alzheimer's disease (Bartus et al., Science 217:408-417 (1982); Fischer et al., Neurobiol. Aging 13:9-23 (1992)), much research has focused on the development of cholinomimetic replacement therapy as a potential treatment of these impairments. Among them, cholinesterase inhibitors, such as physostigmine (Phy) and tetrahydroaminoacridine (THA), have been investigated for memory-enhancing effects in both animals (Rupniak et al., Neurobiol. Aging 11:09-613 (1990); Murray et al. Psychopharmacology 105:134-136 (1991)) and human patients (Mohs et al., J. A. Geriatr. Soc. 33:749-757 (1985); Summers et al., N. Engl. J. Med. 315:1241-1245 (1986)).

Unfortunately, however, the therapeutic usefulness of Physostigmine is limited by its short duration of action, narrow therapeutic window and peripheral cholinergic effects (Pomponi et al., Aging 2:125-153 (1990)). Although oral administration of THA is convenient for clinical use, dose-related hepatotoxicity limits its clinical value (Marx, Science 238:1041-1042 (1987)) and lower, safer doses of THA seem less effective than higher hepatotoxic doses (Gauthier et al., N. Engl. J. Med. 322:1272-1276 (1990).

Further, another cholinesterase inhibitor, heptylphysostigmine (heptyl-Phy), a carbamate derivative of Physostigmine, has also been considered as a candidate for cholinomimetic therapy of cognitive impairments (Brufani et al., Pharmacol. Biochem. Behav. 26:625-629 (1987); Dawson et al., Pharmacol. Blochem. Behav. 39:865-871 (1991); De Sarno et al., Neurochem. Res. 14:971-977, (1989)). This compound appears to have greater lipophilicity, longer inhibitory action on cholinesterase and more persistent increases in acetylcholine in brain with less toxicity than the parent compound (Brufani et al., Pharmacol. Biochem. Behav. 26:625-629 (1987)).

It is also reported that heptyl-Phy facilitates memory consolidation in mice in a passive avoidance test (Brufani et al., Pharmacol. Biochem. Behav. 26:625-629 (1987)), and reverses the performance deficits induced by scopolamine in a range of rodent behavioral tests of long-term and working memory (Dawson et al., Pharmacol Biochem Behav 39:865-871 (1991)). In a recent study, heptyl-Phy attenuated the scopolamine-induced learning impairment of rats in a 14-unit T-maze (Iijima et al., Neurosci Lett (in press 1992)). However, the therapeutic window of heptyl-Phy did not seem wide enough for clinical use.

There is a major problem in this art area regarding acceptable therapeutic windows for highly selective agents active in vivo. In a clinical setting there are variations between patients with regard to handling cholinomimetic agents (i.e., individual differences in absorption, metabolism and excretion, as well as cholinergic dysfunction due to the disease process), which have a strong impact on the efficacy of the drug, and in particular with classes of drugs used in the elderly, the portion of the population that Alzheimer's disease predominantly inflicts.

Such problems present major complications for agents that have a relatively narrow therapeutic window, as optimal dosing is then difficult to achieve. This is particularly true in the elderly, where individual differences in drug handling can be quite large, and affected by the concomitant administration of other drugs for the management of other diseases in the patient. Since many patients needing cholinomimetic therapy are elderly and have other diseases, the problem in this art area is particularly acute.

Accordingly, there is need in the art for highly selective agents active in vivo, having an acceptable therapeutic window, and minimal side effects, for cholinomimetic replacement therapy and treatment of these impairments, which agents have memory-enhancing effects in both animals and human patients.

SUMMARY OF THE INVENTION

It is an object of the present invention to provide an improved method of cholinomimetic therapy for cognitive impairments associated with aging and Alzheimer's disease comprising treating a patient with an effective amount of phenserine, ((−)-N-phenylcarbamoyl eseroline), or a pharmaceutically acceptable salt thereof.

It is another object of the present invention to provide novel pharmaceutically acceptable salts of phenserine, ((−)-N-phenylcarbamoyl eseroline), and pharmaceutical compositions comprising an effective amount of the salts.

It is a further object of the present invention to provide a pharmaceutical composition comprising an effective amount of phenserine, ((−)-N-phenylcarbamoyl eseroline), or a pharmaceutically acceptable salt thereof.

In accordance with these and other objects, the present invention provides pharmaceutical compositions comprising effective amounts of phenserine and its salts, and a method for the treatment of cognitive impairments associated with aging and Alzheimer's disease which comprises treating a patient with an effective amount of phenserine or a pharmaceutically acceptable salt thereof.

BRIEF DESCRIPTION OF THE DRAWINGS

Reference is now made to the drawings accompanying the application wherein.

DESCRIPTION OF THE INVENTION

The present invention provides an improved method of cholinomimetic therapy for cognitive impairments associated with aging and Alzheimer's disease, the method comprising treating a patient with an effective amount of phensezcine, ((−)-N-phenylcarbamoyl eseroline), active or a pharmaceutically acceptable salt thereof. The salts and free base are equally effective. Particularly preferred salts of phenserine are the tartrate, phosphate, and fumarate. By "effective amount" is meant the amount of active administered to the patient, which will be effective to improve the disease condition in the patient.

The present invention also provides novel pharmaceutically acceptable salts of phenserine, ((−)-N-phenylcarbamoyl eseroline), i.e., the tartrate, phosphate, and fumarate salts of phenserine, pharmaceutical compositions comprising an effective amount of the salts being especially preferred.

The present invention also provides pharmaceutical compositions comprising an effective amount of phenserine, ((−)-N-phenylcarbamoyl eseroline), or a pharmaceutically acceptable salt thereof, and a pharmaceutically acceptable carrier or vehicle.

Phenserine, ((−)-N-phenylcarbamoyl eseroline), is a carbamate analog of physostigmine (Phy), which is a long-acting inhibitor of cholinesterase. Phenserine was first prepared by Polonovski, Bull. Soc. Chim. 19, 46–59 (1916), and technical details were summarized by Beilstein, Handbuch der Organischen Chemie, 4th edn. vol 23. Springer Verlag, Berlin, pp 333 (1954)). It was reported in the literature without any stated practical use.

The phenserine compounds of the present invention were prepared from (−)-eseroline and phenylisocyanate as described previously (Brzostowska et al., Med. Chem. Res. (in press 1992)).

The preparation was as follows:

(−)-Eseroline (1), 0.9 g, 4.12 mmol, was dissolved in anhydrous Et$_2$O (90 ml) and several small pieces of Na metal were added (approximately 31 mg). After stirring for about 5 minutes at room temperature under nitrogen, phenylisocyanate (596 mg, 5.03 mmol) was added dropwise. After complete addition, the solvent was evaporated immediately to give a foam (1.25 g weight). This then was recrystallized from EtOAc to give 0.9 g of crystal, phenserine (2). Melting point (uncorrected), measured by Fisher-Johns apparatus, was 142°–143° C. Optical rotation ($[\alpha]_D$, CHCl$_3$), measured by Perkin-Elmer-241 MC automatic polarimeter, was $[\alpha]_D$ −74.2°. IR spectrum (cm$^{-1}$, CHCl$_3$), by Beckman-IR-4230 instrument, was (c=0.5, CHCl$_3$). Thin layer chromatography (silica gel GHLF, 250 μm), solvent system CH$_2$Cl$_2$/5% MeOH, yielded a single spot. Additionally, HPLC analysis using a normal phase narrow bore (2×30 mm) precolumn and an analytical column (2×220 mm, Applied Biosystems), with a mobile phase of 52% 0.01M formic acid, 27% acetonitrile and 21% 0.05M tris buffer (flow rate 0.15 ml/min), and detection by fluorescence (set to 250 nm excitation and 345 emission wavelengths), likewise demonstrated a single peak. Measurement of $^1$H NMR (in CDCl$_3$ with Me$_4$Si as internal reference, δ ppm, J Hz) was δ7.01–7.34 (m, 5H) by Varian XL-300 MHz. Finally, for chemical ionization (CI-MS), using a Finnigan-1015D mass spectrometer, m/z (M$^+$+1) was 338.

The reaction was as follows:

The present invention relates to the clinical value of phenserine and salts for cholinomimetic therapy of cognitive impairments associated with aging and Alzheimer's disease. As described below, phenserine was evaluated for its duration of in vivo activity against rat plasma acetylcholinesterase (AChE), a marker of brain AChE, and its effect on attenuating a scopolamine-induced impairment in learning performance of young rats in a shock-motivated 14-unit T-maze. This is an accepted model for assessing the value of drugs as cognition enhancers in rodents; (D. K. Ingram, Neurobiology of Aging, Vol. 9, pages 475–485, 1988).

Phenserine achieved maximum AChE inhibition of 73.5% at 5 minutes and a maintained a high and relatively constant inhibition for more than 8 hours. For analysis of effects on learning performance, 69 3-month-old male Fischer-344 rats were pretrained in a straight runway to avoid electric foot-shock. On the following day, each animal received 15 trials in the 14-unit T-maze. Sixty minutes prior to the maze training, each rat received the first i.p. injection of either vehicle (Tween 80, ethanol and 0.9% NaCl) or phenserine at 1.5, 3.0, 4.0, 5.0, 7.5, or 10.0 mg/kg. Then 30 minutes prior to training, each animal received a second i.p. injection of either 0.9% NaCl or scopolamine hydrochloride (0.75 mg/kg; SCOP).

Compared to the vehicle-SCOP group, all but 7.5 mg/kg dose of phenserine significantly ameliorated error performance, runtime, shock frequency and shock duration in SCOP-treated rats at the final block of 3 trials. Appearing to have a long effect and a wide therapeutic window, phenserine thus appears very useful as a cognitive enhancer.

Phenserine has a similar potency against human acetylcholinesterase (AChE) as its parent compound, physostigmine (Phy), with IC50 values $24.0 \pm 6.0$ nM vs $27.9 \pm 2.4$ nM, but has poor activity, relative to Physostigmine, against human butyrylcholinesterase (BChE), IC50 values $1300.0 \pm 8.5$ nM vs $16.0 \pm 2.9$ nM (Brzostowska et al. 1992). Hence, phenserine possesses a high selectivity of anticholinesterase action, which appears to be a highly useful property for a centrally acting drug.

AChE and BChE co-exist in brain and peripheral tissues, whereas AChE is responsible for the hydrolysis of ACh and is linked to the neuronal element of the cholinergic system; in brain, BChE is primarily associated with assorted glial cells and is present in a limited manner with the neuronal elements of the nervous system. The roles of BChE remain largely open. There is evidence which supports its involvement in (1) possessing a protective role in the removal of several choline esters formed during cerebral metabolism which otherwise would detrimentally effect AChE and the cholinergic system;

(2) BChE appears to be involved in slow nerve conduction processes;

(3) it possesses a role in lipid and phospholipid metabolism; and (4) it is involved in permeability control and transport of ions across membranes.

The use of long-acting and selective inhibitors of AChE, such as phenserine, represents a cleaner cognition enhancer with less side-effects than previous technology, allowing a wider therapeutic window.

The $LD_{50}$ for Physostigmine is 0.6 mg/kg in the absence of peripheral inhibitors, (Marta et al, Life Sciences 43:1921–1928, 1988). The agent has a low therapeutic windows only inducing cholinesterase inhibition at levels associated with significant side effects. This severely limits its therapeutic value in humans. The toxicity of phenserine, however, is dramatically less. Doses of 20 mg/kg have been administered without peripheral inhibitors and have not been associated with toxicity or deaths. At such high doses, a slight central tremor is evident. Doses of higher than 20 mg/kg phenserine have not been administered to rodents and hence, the $LD_{50}$ of phenserine remains open, but it is substantially higher than that of physostigmine itself.

We have previously demonstrated that the $IC_{50}$ value (inhibition) of brain and plasma AChE and BChE is similar for physostigmine and its analogues and hence, time-dependent inhibition of enzyme can be followed by sequential sampling of plasma. (Atack et al, Journ. Pharm. Exp. Ther. 249:194–202, 1989).

Described below are tests showing the clinical value of phenserine as a cognitive enhancer for the first time by evaluating its duration of in vivo activity and its effects on attenuating a scopolamine-induced impairment in learning performance of young rats in a 14-unit T-maze (Spangler et al., Pharmacol. Biochem. Behav. 25:673–679 (1986)).

As described, this model is a well recognized means for assessing the value of cognition enhancers. It has previously been used to test the value of other physostigmine analogues. Comparative tests demonstrate the best of these (heptyl-physostigmine, Merck, Rahway, N.J.) to be inferior to phenserine. Additionally, physostigmine itself has no significant activity in this model as a consequence of its short pharmacological action.

EXAMPLE 1

Cholinesterase Inhibition

Subjects and procedure. Three-month-old male Fischer-344 rats were anesthetized with Halothane (Ayerst New York, N.Y.). PE 50 catheters, filled with heparinized isotonic saline, were tied into their right femoral artery and vein. Animals then were restrained with a plaster cast that enabled them to move their head and forequarters only and were allowed to recover from anesthesia in a temperature-controlled enclosure. Samples of plasma were removed to measure untreated levels of AChE activity. At 90 minutes after surgery, hexamethonium bromide (5 mg/kg) was administered intraperitoneally, followed by subcutaneous injection of atropine methyl bromide (4 mg/kg) 10 minutes later.

These quaternary nicotinic and muscarinic blocking agents, respectively, do not cross the blood brain barrier and inhibit peripheral cholinergic overdrive, caused by AChE inhibition, which otherwise would be deleterious. At 2 hours after surgery, either 2 mg/kg of Physostigmine or 1 mg/kg of phenserine was administered intravenously. Both were formulated in a manner consistent for intravenous bolus injection. Plasma samples were removed and immediately frozen to −70° C., just prior to intravenous administration of the inhibitors and at times between 2 minutes and 8 hours.

EXAMPLE 2

AChE assay.

Samples were later assayed for AChE activity as described by Atack et al., J. Pharm. Exp. Ther. 249:194–202 (1989)), using the spectrophotometric method of Ellman et al., Biochem. Pharmacol., 7, 88–95 (1961)). Unlike in human plasma, however, AChE and BChE are both present in rat plasma. Therefore, a specific inhibitor of BChE, Iso-OMPA ($1 \times 10-4M$), was used during all determinations of AChE inhibition.

EXAMPLE 3

Behavioral Testing

Subjects. Sixty-nine 3-month-old male Fischer-344 rats (Harlan Splague-Dawley, Indianapolis, Ind.) were used. They were housed doubly in plastic cages in a vivarium maintained at 22° C. and on a 12-hour light/12-hour dark photocycle. Food and water were provided ad libitum. The rats were permitted about 3 weeks acclimation to the vivarium prior to testing.

EXAMPLE 4

Apparatus

A previously described straight runway (Spangler et al., Pharmacol. Biochem. Behav. 25:673–679 (1986)), 2 m long, was used for pretraining in one-way active avoidance. The runway was constructed of clear plastic with a stainless steel grid floor wired to receive a constant- current scrambled electric shock (Model E13-08, Coulbourn Instruments, Lehigh valley, Pa.). Interchangeable black plastic boxes with guillotine doors served as start and goal boxes that could be placed at each end of the runway.

As described in detail previously (Spangler et al. 1986), an automated 14-unit T-maze with a stainless steel grid floor ($2 \times 2$ m), which was wired to a shock source (Model E13-08, Coulbourn Instruments, Lehigh Valley, Pa.), was used for maze training. The maze was separated into five distinct segments by guillotine doors, which prevented the rats from back-tracking into the prior segment.

Infrared photocells located throughout the maze were wired to a microprocessor for electronic recording of errors and runtimes. As in the straight runway, interchangeable black plastic boxes were used as start and goal boxes. Four gray walls surrounded the maze to reduce visual cues. Four audio speakers mounted below the maze provided continuous radio music for masking extraneous sound. The entire maze could be raised to permit cleaning the floor between trials to remove possible odor cues.

EXAMPLE 5

Pretraining (day 1)

For the initial trial, each rat was removed from its home cage, placed into an interchangeable start/goal box, and gently pushed from the box into the straight runway. A successful avoidance was accomplished by moving from the start box to the goal box in 10 sec or less. If the 10-sec avoidance period elapsed, scrambled footshock (0.8 mA) was delivered until the animal escaped to the goal box. Upon goal box entry, a guillotine door was lowered, and the box was moved to a holding area and then to the start area.

After a 2-minute intertrial interval (ITI), the next trial was started. Criterion for completion of straight runway pretraining was 13 correct (no shock) trials out of 15 within a 30-trial maximum, which all rats met successfully.

EXAMPLE 6

Drug Treatment (day b 2)

The animals were taken to the testing room in their home cages 45 minutes prior to injection. The animals were assigned randomly to one of eight treatment groups to receive two i.p. injections. Sixty minutes prior to the maze training, each rat received the first i.p. injection of either vehicle or phenserine in doses ranging from 1.5 to 10.0 mg/kg. Then 30 minutes prior to the training, each animal received a second i.p. injection of either 0.9% NaCl (SAL) or scopolamine hydrochloride (0.75 mg/kg; SCOP).

Phenserine was dissolved in Tween 80/ethanol (3:1, v:v, 15% of the final volume) and then diluted with 0.9% NaCl. All injections were given as a volume of 1 ml/kg. The final group compositions were as follows:

(a) SAL group (n=10) which received vehicle (as first injection)+SAL (as second injection) (this group is represented in FIGS. 2–6 by the solid first histogram column);

(b) SCOP group (n=14), vehicle+SCOP (this group is represented in FIGS. 2–6 by the bold line diagonally cross-hatched second histogram column);

(c) 1.5-PHE group (n=6), phenserine (1.5 mg/kg)+SCOP (this group is represented in FIGS. 2–6 by the inverse video grid third histogram column);

(d) 3.0-PHE group (n=9), phenserine (3.0 mg/kg)+SCOP (this group is represented in FIGS. 2–6 by the diagonally cross-hatched fourth histogram column);

(e) 4.0-PHE group (n=10), phenserine (4.0 mg/kg)+SCOP (this group is represented in FIGS. 2–6 by the blank fifth histogram column);

(f) 5.0-PHE group (n=10), phenserine (5.0 mg/kg) SCOP (this group is represented in FIGS. 2–6 by the solid sixth histogram column);

(g) 7.5-PHE group (n=4), phenserine (7.5 mg/kg)+SCOP (this group is represented in FIGS. 2–6 by the horizontally cross-hatched seventh histogram column);

(h) 10.0-PHE group (n=6), phenserine (10.0 mg/kg)+ SCOP (this group is represented in FIGS. 2–6 by the grid eighth histogram column).

In these studies, no peripheral cholinergic inhibitors were given, as unlike physostigmine, large doses can be administered without toxic side effects.

EXAMPLE 7

Training in the 14-Unit T-Maze (day 2)

As described in detail previously (Spangler et al. Pharmacol. Biochem. Behav. 25:673–679 (1986)), training in the 14-unit T-maze required the rat to move quickly through the maze to avoid footshock by learning 14 position discriminations en route from a start area to the goal box. Briefly, the procedure for the current study was as follows: As in pretraining, on the first trial each rat was removed from its home cage and placed in a start box. Then the animal was gently pushed into the maze, and shock avoidance contingency was set mechanically. To avoid foot-shock in each of 5 maze segments separated by guillotine doors, the animal was required to locomote through a segment beyond the door within 10 sec. If the 10-sec time limit was exceeded, scrambled electric foot shock (0.8 mA) was initiated automatically and continued until the animal passed through the guillotine door. This guillotine door was then lowered, and the shock avoidance contingency for the new segment was reset. A trial was completed when the animal entered the goal box. The goal box containing the animal was moved to a holding area, and then, to the start area. After a 2-minute ITI, the next trial was started. Each animal received one session of 15 trials in the 14-unit T-maze. All training was conducted between 9:00 a.m. and 5:00 p.m.

EXAMPLE 8

Statistical Analysis

The 14-unit T-maze acquisition data comprised five measures: errors (deviations from the correct pathway), alternation errors, runtime,, shock frequency, and shock duration as defined previously (See, Fischer et al., Neurobiol Aging 13:9–23 (1992); Mandel et al., Psychopharmacology 96:421–425 (1988)). Alternation errors refer to errors resulting from the pursuit of an alternation strategy (i.e., an inaccurate sequence of L-R-L or R-L-R turns). Statistical confirmation of the findings was accomplished by analysis of variance (ANOVA) for each maze performance variable at each block (3 trials) of training. Dunnett's tests were conducted to compare the SAL group and each PHE group to the SCOP group as the control ($p<0.05$).

EXAMPLE 9

Results of Cholinesterase Inhibition

Figure 1:
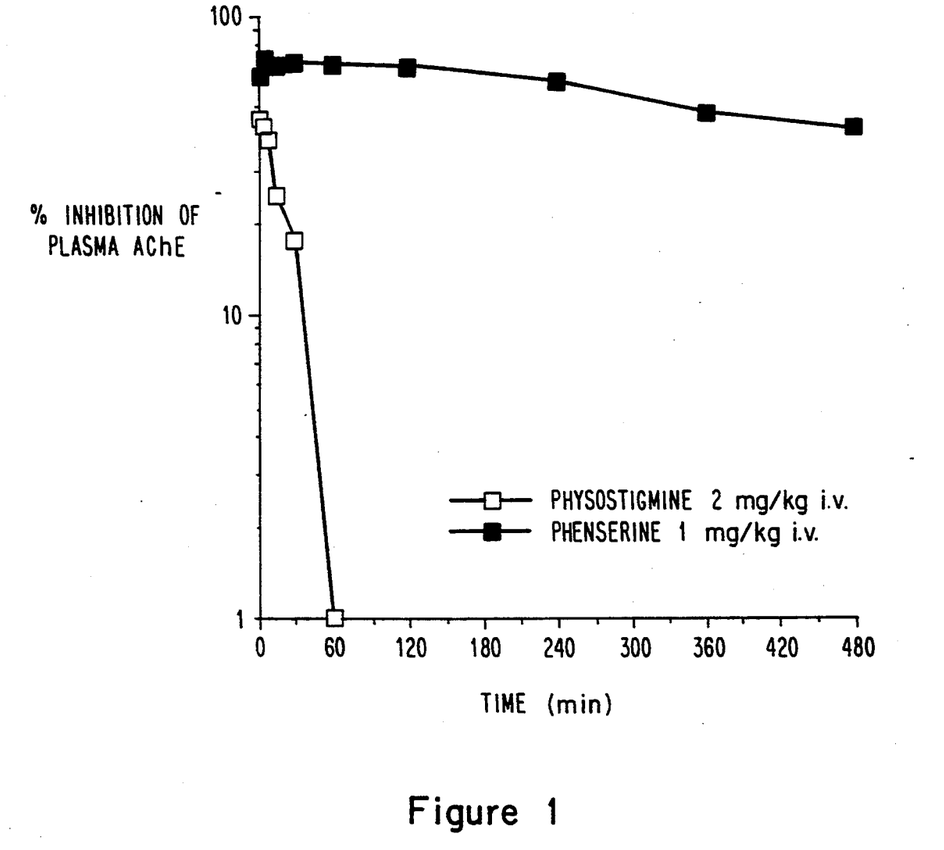
FIG. 1 illustrates the in vivo AChE inhibition by i.v. of physostinine and phenserine in serial samples of plasma from Fisher-344 rats, described in detail below.

As FIG. 1 illustrates, Phyostigmine caused immediate inhibition of plasma AChE of approximately 50% within 2 minutes. Thereafter, enzyme inhibition by Physostigmine declined rapidly and was negligible at 60 minutes. Conversely, phenserine achieved maximum AChE inhibition of 73.5% at 5 minutes and maintained a high and relatively constant inhibition throughout the study, declining to 43.0% inhibition at 8 hours.

EXAMPLE 10

Behavior

Figure 2:
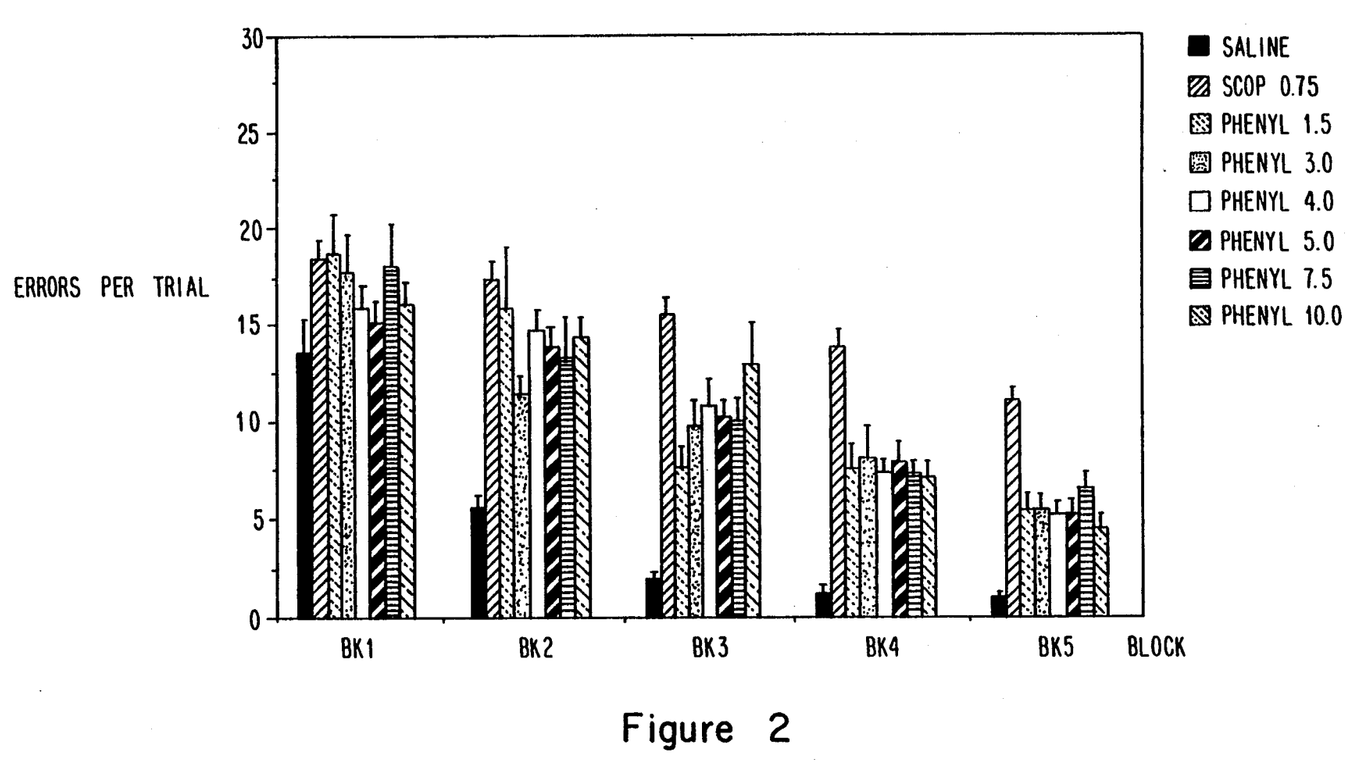
FIG. 2 illustrates the number of errors per trial for blocks of five trials with means and standard errors for specific performance of male Fischer-344 rats in a 14-unit maze, the eight histogram columns for each block being described in detail below.
Figure 3:
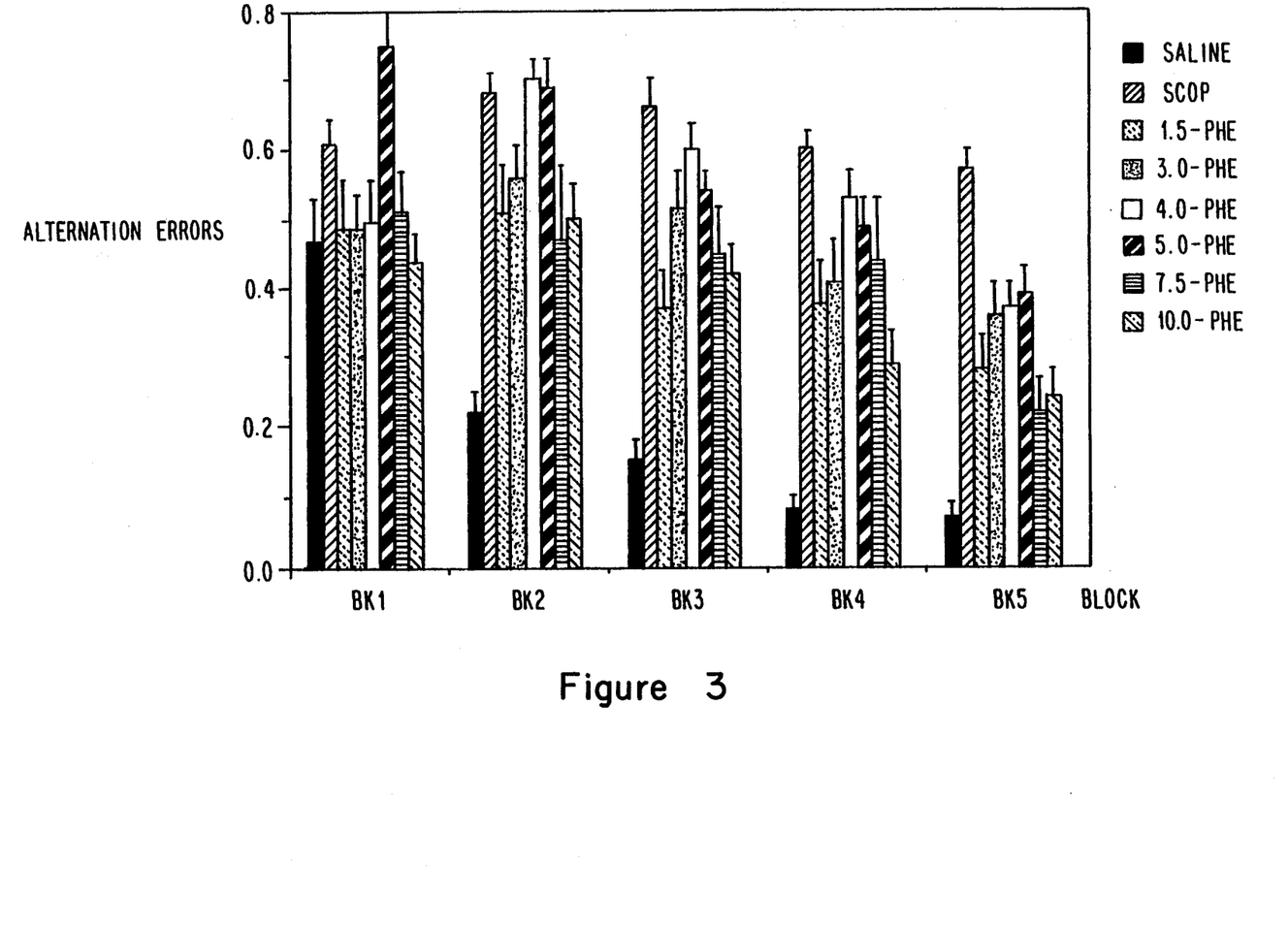
FIG. 3 illustrates the ratio of errors per trial for blocks of five trials with means and standard errors for specific performance of male Fischer-344 rats in a 14-unit maze, the eight histogram columns for each block being described in detail below.

As compared to the SAL group, the SCOP group showed significantly worse performance in all five measures of the maze task at almost all five blocks of trials (FIGS. 2-6). Compared to the SCOP group, all but the 7.5 mg/kg dose of phenserine significantly ameliorated error performance, runtime, shock frequency and shock duration in scopolamine-treated rats at block 5 (FIGS. 2, 4, 5, 6). The number of errors was also reduced significantly at block 4 by all but the 7.5 mg/kg dose of phenserine. Comparing the PHE group to the SAL group, however, there was room for further improvement in all five measures. Concerning alternation errors, only the 10.0 and 1.5 mg/kg doses of phenserine reduced the ratio significantly at blocks 4 and 5 and block 5, respectively (FIG. 3). Rats receiving higher doses of phenserine (7.5 and 10.0 mg/kg) displayed side effects consisting of chewing, grooming, and wet dog shakes. At the dose of 5.0 mg/kg, animals seemed less active than at other doses, and at the dose of 10.0 mg/kg, animals were very aggressive and difficult to handle. However, peripheral cholinergic effects, such as salivation and diarrhea, were not noticed at any doses tested.

EXAMPLE 11

The inhibition of plasma AChE by i.v. bolus administration of phenserine continued for more than 8 hours, while the inhibition by its parent compound Physostigmine declined rapidly and was negligible at 60 minutes. The improvement of learning performance in the 14-unit T-maze was observed more than 1 hour after i.p. administration of phenserine, in contrast with Physostigmine which must be injected 10–15 minutes before behavioral testing (Mandel and Thal, Psychopharmacology 96:421–425 (1988); Murray et al., Psychopharmacology 105:134–136 (1991)). This longer duration of action of phenserine would appear to be an advantage over Physostigmine for clinical use. Physostigmine has a short pharmacological half life in patients which limits its value as a ,cognition enhancer Becker E. Glacobini, Drug Dev. Res. 12:163–195, 1988, and Beller et al, J. Clin. Psychiat. 49:400–404, 1988.

EXAMPLE 12

(−)-Phensezine (100 mg) was dissolved in ether (2 ml) and added with a solution of ferric acid (36 mg) in acetone (2 ml). After standing for twelve hours, the fumarate salt was filtered (90 mg): m.p. 164°–166° C., $[\alpha]_D -74.1°$ (c=0.80, MeOH). To obtain the free base, the fumarate salt (90 mg) was dissolved in water (10 ml), made alkaline by the addition of aqueous ammonia, and extracted with ether (2×10 ml). The combined ether extracts were dried ($Na_2SO_4$) to afford after evaporation of solvent (−)-phenylcarbamoyleseroline, phenserine in form of white needles (62 mg): m.p. 147°–148° C., $[\alpha]_D -80.1°$ (c=1, MeOH).

EXAMPLE 13

The phosphate salt was prepared from (−)-phenylcarbamoyleseroline with phosphoric acid in EtOH and obtained on addition of ether: m.p. 140°–142° C. $[\alpha]_D -72.6°$ (c=0.85, MeOH).

EXAMPLE 14

The tartrate salt of (−)-phenylcarbamoyleseroline was made from the free base in ether by adding a solution of L-(+)-tartaric acid in ethanol: m.p. 143°–145° C., $[\alpha]_D -58.7°$ (c=0.75, MeOH).

Additionally, phenserine produces dramatically higher inhibition of AChE at a lower dose, compared to physostigmine (see FIG. 1).

Thus phenserine significantly attenuated the SCOP-induced learning impairment of rats in a 14-unit T-maze at a wide range of doses, from 1.5 to 10.0 mg/kg. The lack of statistical significance of the 7.5 mg/kg dose was likely associated with the smaller sample size (n=4) in this one group. Cognitive performance deficits in this task induced by this muscarinic antagonism resemble the robust age-related impairments observed in rodents in this task (Ingram et al. 1988). In the same maze, only a 2.0 mg/kg dose of heptyl-Physostigmine delivered an hour in advance of maze training significantly reduced the number of errors, while other doses (1.0, 1.3, 3.0 mg/kg) of heptyl-Physostigmine failed to ameliorate the learning impairment of SCOP-treated rats (Iijima et al., Neurosci Lett (in press 1992)). In rats with nucleus basalis magnocellularis lesions, 0.06 and 0.19 mg/kg of Physostigmine improved water maze performance; however, 0.32 mg/kg of Physostigmine impaired performance (Mandel. et al., Psycho-pharmacology 96:421–425 (1988)). At a dose of 1 mg/kg, THA almost reversed the memory deficits produced by SCOP in an operant delayed non-matching to position task, while a 0.5 mg/kg dose of THA did not improve the SCOP-induced memory deficit, and a dose of 2.5 mg/kg impaired performance in non-treated rats (Murray et al. 1991). The wide therapeutic window of phenserine observed is highly beneficial for clinical use compared to other cholinesterase inhibitors, that presently are in clinical use. These are heptyl-physostigmine and tacrine (THA) whose comparative actions are shown. THA has no activity in similar models and has been shown to induce hepatic toxicity in patients with Alzheimer's disease. This limits its therapeutic potential (Gauthier et al N. Engl. J. Med. 322:1272–1276, 1990; Food & Drug Adminstration, N. Engl. J. Med. 324:349–352, 1991), which have narrow therapeutic windows and wide individual variability in best dose.

All doses of phenserine improved error performance at maze training blocks 4 and 5 except the 7.5 mg/kg dose; however, only 10.0 and 1.5 mg/kg doses of phenserine improved alternation error performance at blocks 4 and 5 and block 5, respectively. Most of the phenserine-treated animals continued to use an alternation strategy for solving the maze. Rats with fimbria-fornix lesions or hippocampal damage as well as SCOP administration exhibit prevalent use of an alternation strategy in this maze (Bresnahan et al. Psychobiology 16:243–250 (1988); Spangler et al., Pharmacol. Biochem. Behav. 25:673–679 (1986)). The ability of phenserine to impartness improvement in alternation error performance than in error performance resembles results obtained in our study of heptyl-Phy (Iijima et al. (in press 1992)). The lack of improvement in heptyl-Phy-treated rats in this aspect of cognitive performance was attributed to the possibility that heptyl-Phy might exert its clinical effects through cholinesterase inhibition in the neocortex rather than in the hippocampus (Iijima et al. (in press 1992)).

The above results indicate long-acting effects and a wide therapeutic window of activity for phenserine. Thus the present invention relates to an improved method for cholinomimetic therapy of cognitive impairments associated with aging and Alzheimer's disease using effective amounts of phenserine and its salts.

Comparative Example

For comparative studies, the duration and amount of AChE inhibition of phenserine was compared to that of THA (tacrine). The latter has been utilized in clinical trials as a cognition enhancer and was reported to show cognitive benefits in patients with Alzheimer's disease (Summers et al, Biol. Psychiatry 16:145–153, 1981). The same technique was utilized for previous studies discussed herein. THA was dissolved in Tween 80/ethanol and then diluted with 0.1 m $Na_3PO_4$ (pH 8.0) butter. THA demonstrated maximal inhibition of AChE of approximately 33% at 2 minutes. This rapidly declined and was maintained at less than 20% within 5 minutes. This meager inhibition of AChE was only obtained at a very high dose of 10 mg/kg THA. Adminstration of lower doses (5 mg/kg, I.V.) did not result in measurable inhibition of AChE in rats, whereas adminstration of higher doses (20 mg/kg, I.V.) resulted in the death of more than 50% of the animals.

Hence, with regard to AChE inhibition and duration of inhibition, phenserine compares highly favorably to THA. Phenserine induces long, steady state inhibition of AChE at very low and non-toxic doses. Recent studies in Alzheimer's patients indicate that THA likewise causes toxicity, as such high doses are required to cause significant AChE inhibitors (Food & Drug Adminstration. N. Engl. J. Med. 324:349–352, 1991).

Surprisingly, the carbamate according to the present invention have shown high potency. Thus, the phenyl-carbamate and its derivative salts according to the present invention are .longer lasting and appear to be less toxic than other carbamate analogues in this art. Accordingly, the improved method for treating cognitive disorders using compounds according to the present invention represent a significant advancement over the prior art.

Compositions within the scope of the invention include compositions wherein the active ingredient is contained in an effective amount to achieve its intended purpose. Effective concentrations may range from 0.001 wt. % to 1.0 wt, %. The compounds can be administered in any pharmaceutically acceptable amount, for example, in amounts ranging from 0.001 gram to about 1 gram per kilogram of body weight. Based on the information which is presented herein, the determination of effective amounts is well within the skill of the ordinary practitioner in the art.

The compounds are generally used in pharmaceutical compositions (wt %) containing the active ingredient with a carrier or vehicle in the composition in an amount of about 0.1 to 99 wt % and preferably about 25–85 wt %. The compounds may be administered in any desired form, including parenterally, orally, injection, or by suppository using known methods.

Either fluid or solid unit dosage forms can be readily prepared for oral administration. For example, the active compounds can be admixed with conventional ingredients such as dicalcium phosphate, magnesium aluminum silicate, magnesium stearate, calcium sulfate, starch, talc, lactose, acacia, methyl cellulose and functionally similar materials as pharmaceutical excipients or carriers. A sustained release formulation may optionally be used. In older or incoherent patients sustained release formulations may even be preferred. Capsules may be formulated by mixing the compound with a pharmaceutical diluent which is inert and inserting this mixture into a hard gelatin capsule having the appropriate size. If soft capsules are desired, a slurry of the compound with an acceptable vegetable, light petroleum or other inert oil can be encapsulated by forming into a gelatin capsule.

Suspensions, syrups and elixirs may be used for oral administration of fluid unit dosage forms. A fluid preparation including oil may be used for oil soluble forms. A vegetable oil such as corn oil, peanut oil or sunflower oil, for example, together with flavoring agents, sweeteners and any preservatives produces an acceptable fluid preparation. A surfactant may be added to water to form a syrup for fluid unit dosages. Hydro-alcoholic pharmaceutical preparations may be used having an acceptable sweetener (such as sugar, saccharin, or a biological sweetener) and a flavoring agent in the form of an elixir.

Pharmaceutical compositions for parenteral and suppository administration can also be obtained using techniques standard in the art.

Preferred uses of the compounds according to the invention are as pharmaceutical agents suitable for oral administration. Another preferred use of the compounds is in transdermal parenteral formulations, which are particularly useful in treating cholinergic disorders such as glaucoma, Myasthenia Gravis, Alzheimer's disease, and organophosphate poisoning. Accordingly, compositions suitable for administration to these areas are particularly included within the invention. The above parenteral solutions or suspensions may be administered transdermally and delivered with a skin patch. If desired they may be given by injection in an appropriate vehicle such as sesame oil.

Accordingly, incorporation of the active compounds and a slow release matrix may be implemented for administering transdermally. The compounds may be administered transdermally in amounts of about 0.01 to 99% of the composition and preferably about 25 to 85 wt % of the active ingredient in the vehicle or carrier.

Transdermal therapeutic systems are self-contained dosage forms that, when applied to intact skin, deliver drug (s) at a controlled rate to the systemic circulation. Advantages of using the transdermal routing include: enhanced therapeutic efficacy, reduction in the frequency of dosing, reduction of side effects due to optimization of blood-concentration vs. time profile, increased patient compliance due to elimination of multiple dosing schedules, bypassing the hepatic "first pass" metabolism, avoiding gastro-intestinal incompatibilities and providing a predictable and extendable duration of activity. However, the main function of the skin is to act as a barrier to entering compounds. As a consequence, transdermal therapy has been preferred for a limited number of drugs that possess the desirable physicochemical properties for diffusion across the skin barrier. One effective method of overcoming the barrier function of the skin is to include a penetration enhancer in the formulation of the transdermal therapeutic system.

The penetration enhancer is a chemical compound that, when included in a formulation, temporarily increases the permeability of the skin to a drug line allowing more of the drug to be absorbed in a shorter period of time. Several different types of penetration enhances have been reported such as dimethylsulfoxide, n-decylmethylsulfoxide, N,N-dimethylacetamide, N,N-dimethylformamide, 1-dodecylazacycloheptane-2-one (Azone), propylene glycol, ethanol, pyrrolidones such as N-methyl-2-pyrrolidone (NMP) and surfactants.

The above compounds can be present in the reservoir alone or in combination with pharmaceutical carriers. The pharmaceutical carriers acceptable for the purposes of this invention are the known art carriers that do not adversely effect the drug, the host, or the material comprising the drug delivery device. Suitable pharmaceutical carriers include sterile water, saline, dextrose, dextrose in water or saline condensation products of castor oil and ethylene oxide combining about 30 to 35 moles of ethylene oxide per mole of castor oil, liquid acid, lower alkanols, oils such as corn oil, peanut oil, sesame oil and the like, with emulsifiers such as mono- or di-glyceride of a fatty acid; or a phosphatide, e.g., lecithin, and the like; glycols, polyalkylene glycols, aqueous media in the presence of a suspending agent, for example, sodium carboxymethyl cellulose, sodium alginate, poly(vinylpyrrolidone), and the like, alone, or with suitable dispensing agents such as lecithin, polyoxyethylene stearate, and the like. The carrier may also contain adjuvants such as preserving agents, stabilizing agents, wetting agents, emulsifying agents and the like together with penetration enhancer and the compounds of this invention.

The effective dose for mammals may vary due to such factors as age, weight, activity level or condition of the subject being treated. Typically, an effective dosage of a compound according to the present invention is about 1 to 800 milligrams when administered by either oral or rectal dose from 1 to 3 times daily. This is about 0.002 to about 50 milligrams per kilogram of the subject's weight administered per day. Preferably about 10 to about 300 milligrams are administered orally or rectally 1 to 3 times a day for an adult human. The required dose is considerably less when administered parenterally. Preferably about 0.01 to about 150 milligrams may be administered intramuscularly or transdermally, one or two times a day for an adult human.

Compounds of the present invention may be administered topically in amounts of about 0.01 to about 99 wt % of the composition, and preferably about 25 to 85 wt %. The present compounds are also useful in a method for treating cholinergic disorders such as glaucoma, Myasthenia Gravis, Alzheimer's disease, and as an antidote against poisoning with organo phosphates. The method according to the invention comprises administering an effective amount of a compound according to the invention or an effective amount of a pharmaceutical composition according to the invention to a mammal in need of such treatment.

DETAILED DESCRIPTION OF THE DRAWINGS

FIG. 1 illustrates the in vivo AChE inhibition by i.v. physostigmine and phenserine in serial samples of plasma from Fischer-344 rats. It shows that Physostigmine caused immediate inhibition of plasma AChE of approximately 50% within 2 minutes. Thereafter, enzyme inhibition declined rapidly and was negligible at 60 minutes. Conversely, it shows that phenserine achieved maximum AChE inhibition of 73.5% at five minutes and maintained a high and relatively constant inhibition for more than 8 hours.

FIG. 2 illustrates the number of errors per trial for blocks of five trials with means and standard errors for specific performance of male Fischer-344 rats in a 14-unit maze; the eight histogram columns for each block from left to right represent eight treatment compositions, i.e., (a) SAL group (n=10) which received vehicle (as first injection)+SAL (as second injection); (b) SCOP group (n=14), vehicle+SCOP; (c) 1.5-PHE group (n=6), phenserine (1.5 mg/kg)+SCOP; (d) 3.0-PHE group (n=9), phenserine (3.0 mg/kg)+SCOP; (e) 4.0-PHE group (n=10), phenserine (4.0 mg/kg)+SCOP; (f) 5.0-PHE group (n=10), phenserine (5.0 mg/kg)+SCOP; (g) 7.5-PHE group (n=4), phenserine (7.5 mg/kg)+SCOP; (h) 10.0-PHE group (n=6), phenserine (10.0 mg/kg)+SCOP.

FIG. 3 illustrates the ratio of errors per trial for blocks of five trials with means and standard errors for specific performance of male Fischer-344 rats in a 14-unit maze, the eight histogram columns for each block are as described for FIG. 2, above.

Figure 4:
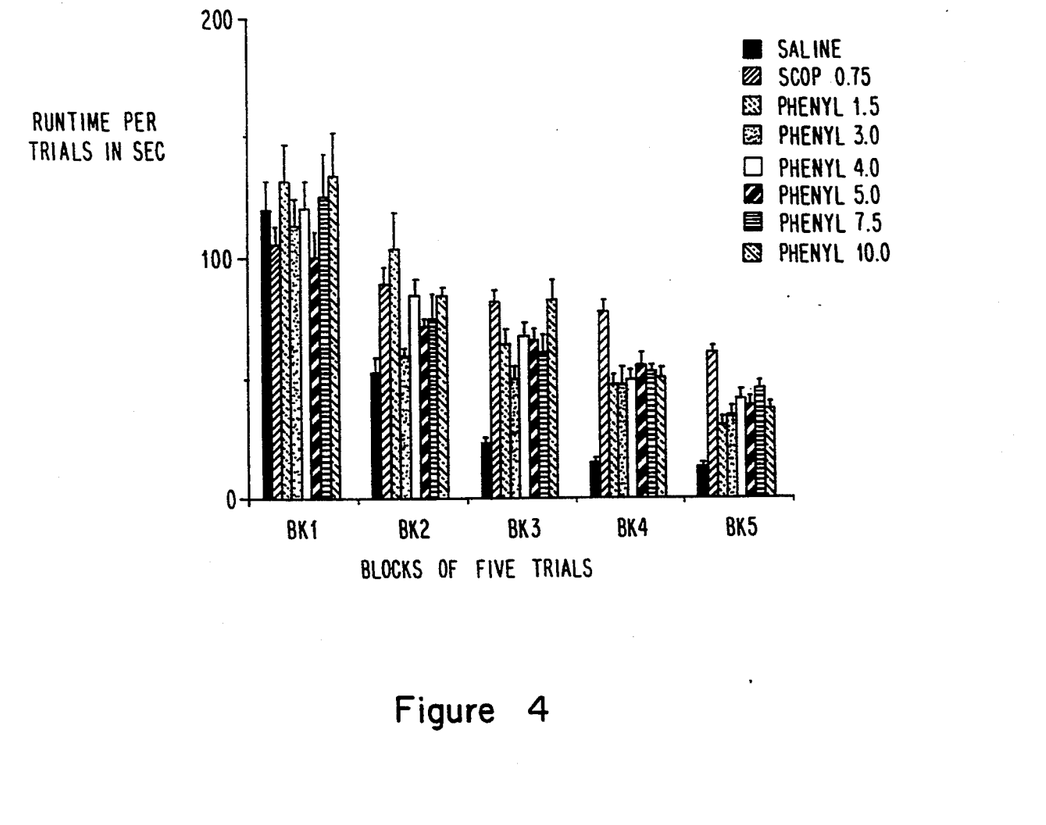
FIG. 4 illustrates the run time in seconds per trial for blocks of five trials with means and standard errors for specific performance of male Fischer-344 rats in a 14-unit maze, the eight histogram columns for each block being described in detail below.

FIG. 4 illustrates the run time in seconds per trial for blocks of five trials with means and standard errors for specific performance of male Fischer-344 rats in a 14- unit maze, the eight histogram columns for each block are as described for FIG. 2, above.

Figure 5:
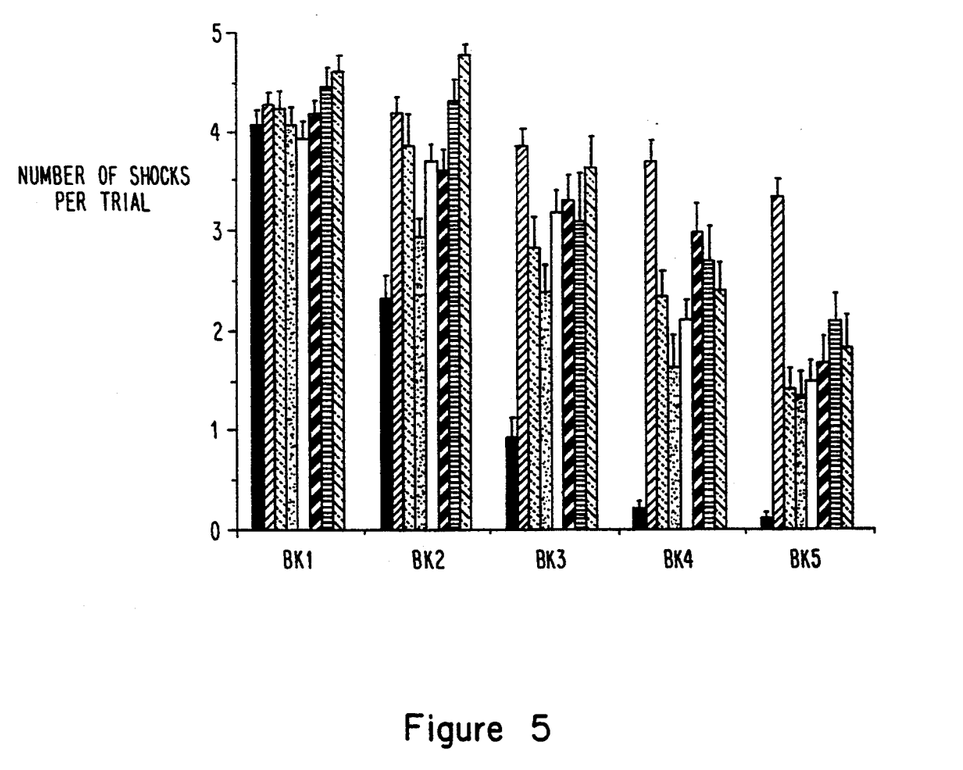
FIG. 5 illustrates the number of shocks per trial for blocks of five trials with means and standard errors for specific performance of male Fischer-344 rats in a 14-unit maze, the eight histogram columns for each block being described in detail below.

FIG. 5 illustrates the number of shocks per trial for blocks of five trials with means and standard errors for specific performance of male Fischer-344 rats in a 14-unit maze, the eight histogram columns for each block are as described in FIG. 2, above.

Figure 6:
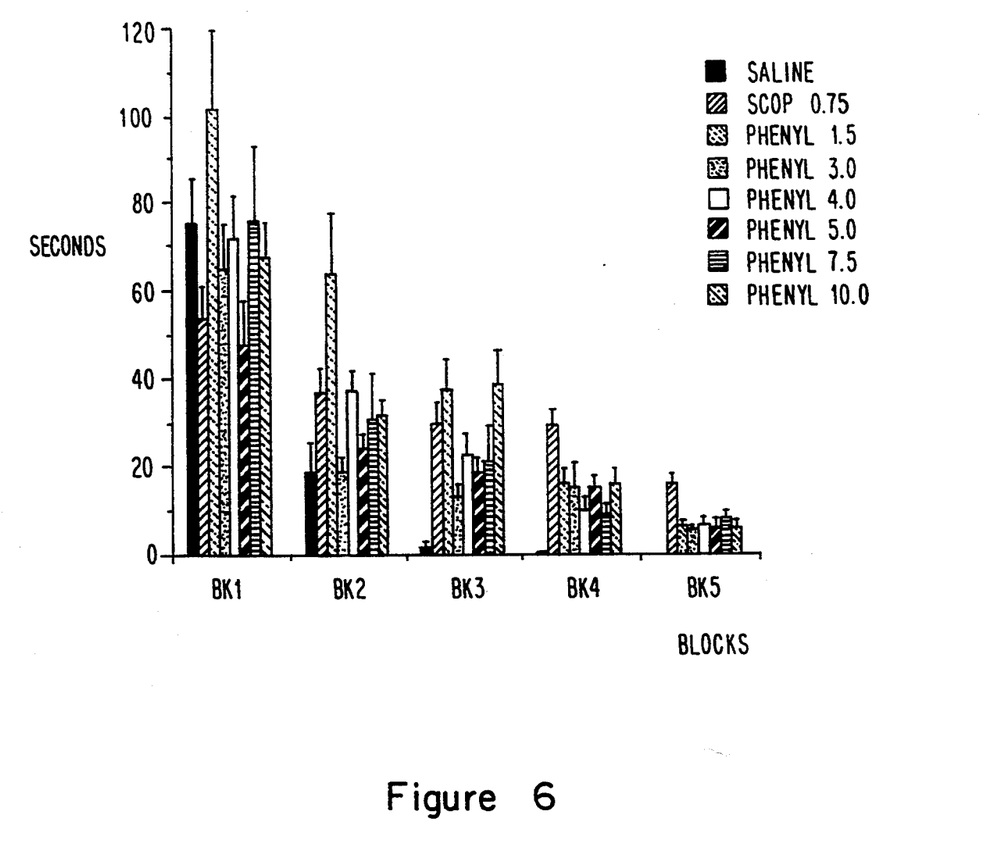
FIG. 6 illustrates the shock duration per trial in seconds for blocks of five trials with means and standard errors for specific performance of male Fischer-344 rats in a 14-unit maze, the eight histogram columns for each block being described in detail below.

FIG. 6 illustrates the shock duration per trial in seconds for blocks of five trials with means and standard errors for specific performance of male Fischer-344 rats in a 14-unit maze, the eight histogram columns for each block are as described in FIG. 2, above.

Figure 7:
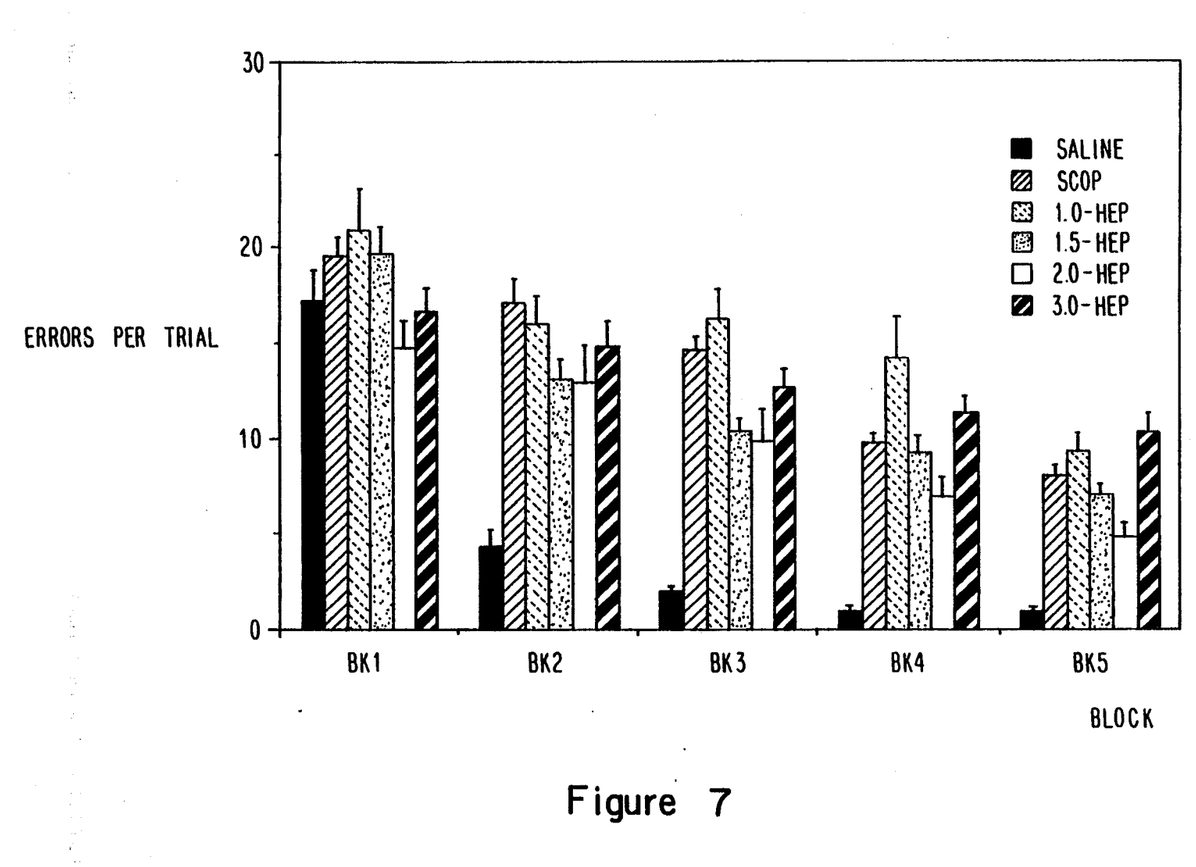
FIG. 7 illustrates the mean errors per trial at each block of three trials where SCOP-treated rats exhibited impaired performance relative to the SAL group and the 2.0-heptyl-Phy group demonstrated reduced error performance compared to the SCOP group.

FIG. 7 illustrates the mean errors per trial at each block of three trials where SCOP-treated rats exhibited impaired performance relative to the SAL group and the 2.0-heptyl-Phy group demonstrated reduced error performance compared to the SCOP group.

Figure 8:
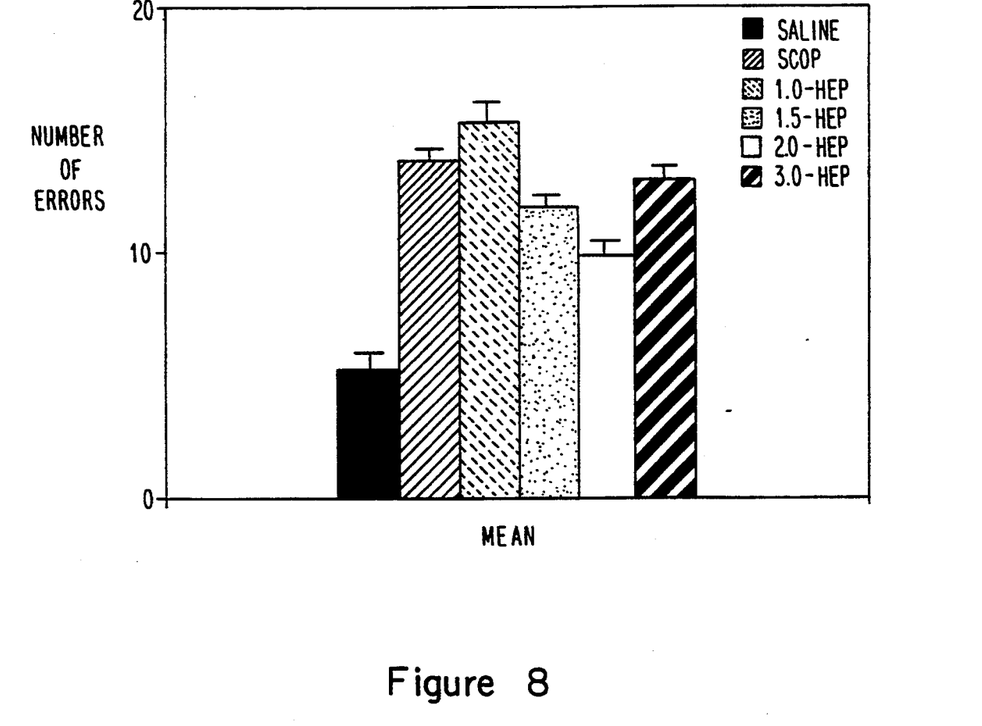
FIG. 8 illustrates the mean ($\pm$SE) errors per trial for 15 trials; the 2.0-heptyl-Phy group showed significantly ($P<0.05$) better performance than the SCOP group.

FIG. 8 illustrates the mean ($\pm$SE) errors per trial for 15 trials; the 2.0-heptyl-Phy group showed significantly ($P<0.05$) better performance than the SCOP group.

Figure 9:
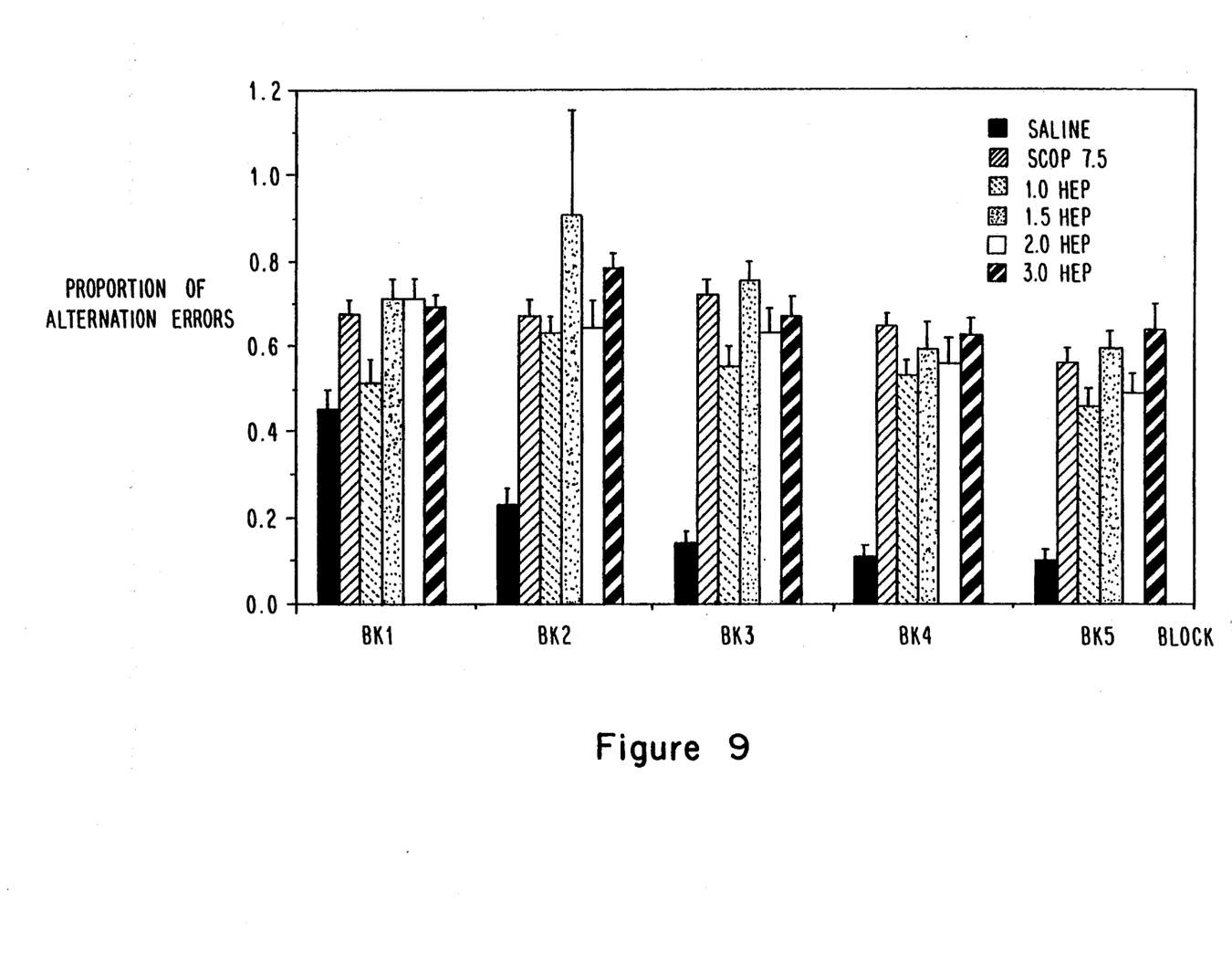
FIG. 9 illustrates the mean ratio of alternation errors per trial at each block of three trials to the frequency of opportunities to make alternation errors, which shows heptyl-Phy treatment had no significant effect of the SCOP-treated rat's tendency to make errors resulting from an alternation strategy.

FIG. 9 illustrates the mean ratio of alternation errors per trial at each block of three trials to the frequency of opportunities to make alternation errors, which shows heptyl-Phy treatment had no significant effect of the SCOP-treated rat's tendency to make errors resulting from an alternation strategy.

The foregoing description of the specific embodiments will so fully reveal the general nature of the invention that others can, by applying current knowledge, readily modify and/or adapt for various applications such specific embodiments without departing from the generic concept and therefore such adaptations are intended to be comprehended within the meaning and range of equivalents of the disclosed embodiments. It is to be understood that the phraseology or terminology employed herein is for the purpose of description only and not of limitation.

What is claimed is:

1. A method of conducting cholinomimetic therapy to treat cognitive impairments associated with aging or Alzheimer's disease which comprises treating a patient having said cognitive impairment with an effective amount of phenserine, or a pharmaceutically acceptable salt thereof.

2. A method according to claim 1, wherein the pharmaceutically acceptable salt is selected from the group consisting of the tartrate, phosphate, and fumarate salt.

3. A method according to claim 1, wherein the effective amount ranges from 0.001 gram to 1 gram per kilogram of body weight of the patient.

4. A method for the treatment of Alzheimer's disease in human which comprises adminstration of a pharmaceutical composition to said human comprising an effective amount of phenserine or a pharmaceutically acceptable salt thereof as the effective ingredient.

5. A method according to claim 4, wherein the pharmaceutically acceptable salt is selected from the group consisting of the tartrate, phosphate, and fumarate salt.

6. A method according to claim 5, wherein the effective amount ranges from 0.001 gram to 1 gram per kilogram of body weight of the human.

* * * * *

UNITED STATES PATENT AND TRADEMARK OFFICE
CERTIFICATE OF CORRECTION

PATENT NO. : 5,409,948
DATED : April 25, 1995
INVENTOR(S) : Nigel H. Greig et al.

It is certified that error appears in the above-identified patent and that said Letters Patent is hereby corrected as shown below:

Title page,
Item [*] Notice, delete "The portion of the term of this patent subsequent to December 15, 2009 has been disclaimed" and replace with -- The portion of the term of this patent subsequent to the expiration of U.S. Patent No. 5,171,750 has been disclaimed --.

Signed and Sealed this

Seventh Day of February, 2006

JON W. DUDAS
*Director of the United States Patent and Trademark Office*